United States Patent
Thörne et al.

(10) Patent No.: US 9,220,871 B2
(45) Date of Patent: Dec. 29, 2015

(54) NEEDLE SHIELDING PAWL STRUCTURES

(75) Inventors: Johan Fredrik Thörne, Helsingborg (SE); Lars-Åke Lennart Larsson, Lund (SE); Kristoffer Glowacki, Staffanstorp (SE); Jörgen Bruno Hager, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 825 days.

(21) Appl. No.: 11/943,345

(22) Filed: Nov. 20, 2007

(65) Prior Publication Data
US 2008/0140004 A1 Jun. 12, 2008

Related U.S. Application Data

(60) Provisional application No. 60/867,046, filed on Nov. 22, 2006.

(51) Int. Cl.
*A61M 25/06* (2006.01)
*A61M 5/32* (2006.01)

(52) U.S. Cl.
CPC ........ *A61M 25/0606* (2013.01); *A61M 25/0625* (2013.01); *A61M 25/0637* (2013.01); *A61M 5/3275* (2013.01); *A61M 2005/325* (2013.01)

(58) Field of Classification Search
CPC .......... A61M 5/3275; A61M 25/0606; A61M 25/0625; A61M 25/0637; A61M 2005/325
USPC ............... 604/110, 162, 163, 164.01, 164.08, 604/192, 198, 263, 264
See application file for complete search history.

(56) References Cited

U.S. PATENT DOCUMENTS

| 4,929,241 A | 5/1990 | Kulli |
| 4,952,207 A | 8/1990 | Lemieux |
| 4,970,998 A * | 11/1990 | Tyler ........................ 123/185.3 |
| 4,978,344 A | 12/1990 | Dombrowski et al. |

(Continued)

FOREIGN PATENT DOCUMENTS

WO WO 2004/065713 A1 8/2004

OTHER PUBLICATIONS

"Popular Bender Options." Danly UK Limited. Oct. 10, 2005.*

(Continued)

*Primary Examiner* — Nathan R Price
(74) *Attorney, Agent, or Firm* — Jeanne Lukasavage; Craig Metcalf; Kirton McConkie

(57) ABSTRACT

An extravascular system is provided which includes a catheter assembly and a needle assembly. The needle assembly includes a needle cap containing a needle shield. The needle shield may be a V-clip having a pawl. The pawl may communicate with an extension on the needle shield by forming a bend between the pawl and the extension. The bend may include at least one dent, and the dent may be formed within the center of the bend. Alternatively, the bend may include a plurality of dents. The plurality of dents may be placed at various locations over the pawl width. The pawl may be folded back onto itself. Indeed, the pawl may be folded back on itself to form essentially a pawl of double thickness. In addition, the pawl may be constructed with a bend of various angles. The angle of the bend between the pawl and the extension may be less than 90°. The angle may be in the range of from about 90° and about 70°. The pawl may also include a corrugated design or structure.

13 Claims, 8 Drawing Sheets

(56) References Cited

U.S. PATENT DOCUMENTS

| | | |
|---|---|---|
| 5,051,109 A | 9/1991 | Simon |
| 5,053,017 A | 10/1991 | Chamuel |
| 5,135,504 A | 8/1992 | McLees |
| 5,215,528 A | 6/1993 | Purdy et al. |
| 5,279,591 A | 1/1994 | Simon |
| 5,322,517 A | 6/1994 | Sircom et al. |
| 5,328,482 A | 7/1994 | Sircom et al. |
| 5,419,766 A | 5/1995 | Chang et al. |
| 5,458,658 A | 10/1995 | Sircom |
| 5,533,974 A | 7/1996 | Gaba |
| 5,562,633 A | 10/1996 | Wozencroft |
| 5,662,610 A | 9/1997 | Sircom |
| 5,697,907 A | 12/1997 | Gaba |
| 5,718,688 A | 2/1998 | Wozencroft |
| 5,823,997 A | 10/1998 | Thorne |
| 5,853,393 A | 12/1998 | Bogert |
| 5,951,515 A | 9/1999 | Osterlind |
| 6,056,726 A | 5/2000 | Isaacson |
| 6,117,108 A | 9/2000 | Woehr et al. |
| 6,234,999 B1 | 5/2001 | Wemmert et al. |
| 6,287,278 B1 | 9/2001 | Woehr et al. |
| 6,322,537 B1 | 11/2001 | Chang |
| 6,443,929 B1 | 9/2002 | Kuracina et al. |
| 6,616,630 B1 | 9/2003 | Woehr et al. |
| 6,620,136 B1 | 9/2003 | Pressly, Sr. et al. |
| 6,629,959 B2 | 10/2003 | Kuracina et al. |
| 6,641,555 B1 | 11/2003 | Botich et al. |
| 6,652,486 B2 | 11/2003 | Bialecki et al. |
| 6,692,471 B2 | 2/2004 | Boudreaux |
| 6,702,595 B2 | 3/2004 | Nelson et al. |
| 6,709,419 B2 | 3/2004 | Woehr |
| 6,749,588 B1 | 6/2004 | Howell et al. |
| 6,860,871 B2 | 3/2005 | Kuracina et al. |
| 6,981,965 B2 | 1/2006 | Luther et al. |
| 7,018,344 B2 | 3/2006 | Bressler et al. |
| 7,097,633 B2 | 8/2006 | Botich et al. |
| 7,160,269 B2 | 1/2007 | Woehr |
| 7,186,239 B2 | 3/2007 | Woehr |
| 7,201,740 B2 | 4/2007 | Crawford |
| 7,214,211 B2 | 5/2007 | Woehr et al. |
| 7,226,434 B2 | 6/2007 | Carlyon et al. |
| 7,238,169 B2 | 7/2007 | Takagi et al. |
| 7,264,613 B2 | 9/2007 | Woehr et al. |
| 2002/0169418 A1 | 11/2002 | Menzi et al. |
| 2003/0114797 A1 | 6/2003 | Vaillancourt et al. |
| 2003/0144627 A1 | 7/2003 | Woehr et al. |
| 2003/0167062 A1 | 9/2003 | Gambale et al. |
| 2003/0199827 A1 | 10/2003 | Thorne |
| 2003/0228808 A1 | 12/2003 | Nelson et al. |
| 2004/0010227 A1 | 1/2004 | Riesenberger et al. |
| 2004/0049155 A1 | 3/2004 | Schramm |
| 2004/0162525 A1 | 8/2004 | Vaillancourt et al. |
| 2004/0225260 A1 | 11/2004 | Villa et al. |
| 2004/0243061 A1 | 12/2004 | McGurk |
| 2005/0027263 A1 | 2/2005 | Woehr et al. |
| 2005/0070855 A1 | 3/2005 | Ferguson et al. |
| 2005/0080378 A1 | 4/2005 | Cindrich et al. |
| 2005/0182362 A1 | 8/2005 | Sircom et al. |
| 2006/0074384 A1 | 4/2006 | Kohler |
| 2006/0116638 A1 | 6/2006 | Woehr et al. |
| 2006/0270980 A1 | 11/2006 | Menzi et al. |
| 2007/0038179 A1 | 2/2007 | Bialecki et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0038188 A1 | 2/2007 | Bialecki et al. |
| 2007/0073221 A1 | 3/2007 | Bialecki et al. |
| 2007/0073222 A1 | 3/2007 | Lilley, Jr. et al. |
| 2007/0129689 A1 | 6/2007 | Woehr et al. |
| 2007/0156093 A1 | 7/2007 | Woehr |
| 2007/0161950 A1 | 7/2007 | Carlyon et al. |
| 2007/0179447 A1 | 8/2007 | Carrez et al. |

OTHER PUBLICATIONS

"Can anyone help me with sheet metal bending?" Post # 6, dated Jun. 13, 2006. Retrieved from http://www.3dcadforums.com/solidworks-forum/448-can-anyone-help-me-sheet-metal-bending.html on Jan. 28, 2015.*

* cited by examiner

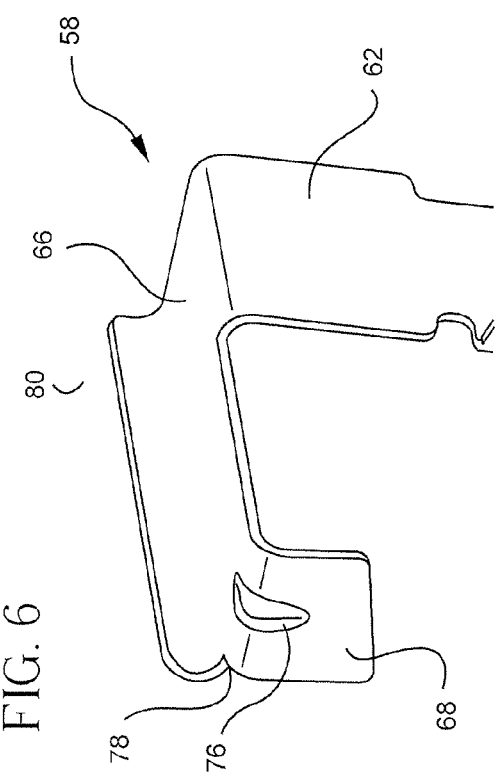
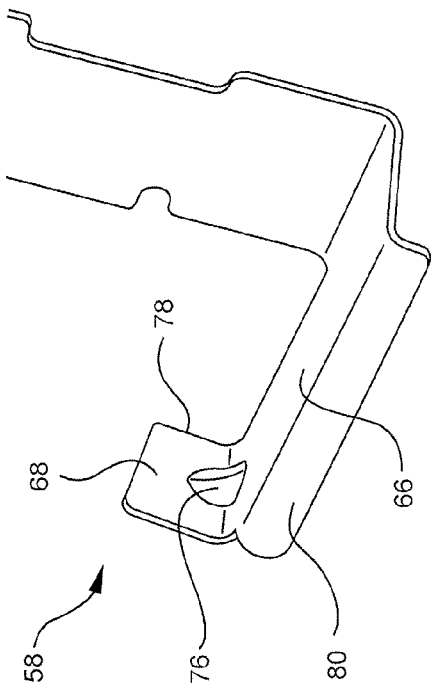

NEEDLE SHIELDING PAWL STRUCTURES

RELATED APPLICATIONS

This application claims the benefit of U.S. Provisional Application No. 60/867,046, filed Nov. 22, 2006, entitled NEEDLE TIP SHIELD, which is incorporated herein by reference.

BACKGROUND OF THE INVENTION

This invention relates generally to vascular access devices and methods, including catheter assemblies and devices used with catheter assemblies. Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber of the catheter assembly. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield device that covers the needle tip and prevents accidental needle sticks. In general, a needle shield includes a housing, a sleeve, or other similar device that is designed such that when the needle is withdrawn from the patient, the needle tip will be trapped/captured within the needle tip shield. The purpose of these needle tip shield devices is to house the tip of the needle in a secure location, thereby avoiding the possibility of needle sticks after the needle and needle shield device are separated from the catheter, which is left in place to provide intravenous access to the patient.

Various systems and methods are needed to provide needle tip shields that optimally secure to and separate from the remainder of a catheter assembly and provide adequate protection from the tip of a needle during and after needle use.

BRIEF SUMMARY OF THE INVENTION

The present invention has been developed in response to problems and needs in the art that have not yet been fully resolved by currently available vascular access systems and methods. Thus, these systems and methods are developed to provide more efficient vascular access systems and methods capable of ensuring proper needle tip shield function.

An extravascular system for accessing the vasculature of a patient may include a catheter, a needle disposed within the catheter, and a needle tip shield assembly. The catheter may include a groove and/or other means of attaching to another vascular access device within the extravascular system. The needle may be disposed within the catheter. The needle tip shield assembly may include a needle cap, the needle cap may include a needle shield, and the needle shield may include a pawl. The pawl may be reinforced and engage with the groove or other means of attachment of the catheter to secure the needle tip shield to the catheter. The reinforced pawl avoids, limits, and/or minimizes premature separation from the groove.

The needle shield may be a V-clip. The pawl may communicate with an extension on the needle shield by forming a bend between the pawl and the extension. The bend may include at least one dent, and the dent may be formed within the center of the bend. Alternatively, the bend may include a plurality of dents. The plurality of dents may be placed at various locations over the pawl width. The pawl may be folded back onto itself. Indeed, the pawl may be folded back on itself to form essentially a pawl of double thickness.

In addition, the pawl may be constructed with a bend of various angles. The angle of the bend between the pawl and the extension may be less than 90°. The angle may be in the range of from about 90° and about 70°. The pawl may also include a corrugated design or structure.

A method of engaging a vascular access device to another vascular access device within an extravascular system may include providing a catheter, providing a needle, and providing a needle tip shield assembly. The step of providing a catheter may include providing a catheter defining a groove or other means of attaching to another vascular access device. The step of providing a needle may include providing a needle disposed within the catheter. The step of providing a needle tip shield assembly may include providing a needle tip shield assembly having a needle cap where the needle cap may have a needle shield and the needle shield may have a pawl. The method may also include reinforcing the pawl, securing the needle tip shield to the catheter by engaging the pawl with the groove of the catheter, and/or avoiding premature separation of the pawl from the groove. The needle shield may be a V-clip.

The method may also include providing an extension on the needle shield and forming a bend between the pawl and the extension. The method may also include denting the bend, forming at least one dent in the bend, denting the center of the bend, folding the pawl back onto itself, forming the bend between the pawl and the extension at an angle that is less than 90 degrees, such as in the range of from about 90 degrees to about 70 degrees, bending the pawl in a corrugated design, and/or forming the pawl into a corrugated design.

An extravascular system for accessing the vasculature of a patient may include a catheter having a first means for engaging, a needle disposed within the catheter, and a needle tip shield assembly. The needle tip shield assembly may have a needle cap, the needle cap may have a needle shield, and the needle shield may have a second means for engaging. The second means for engaging may be reinforced and may engage with the first means for engaging to secure the needle tip shield to the catheter. The reinforced second means for engaging may avoid premature separation from the first means for engaging.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 6 is a top perspective view of a pawl having a dent.

FIG. 7 is a bottom perspective view of the pawl of FIG. 6.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
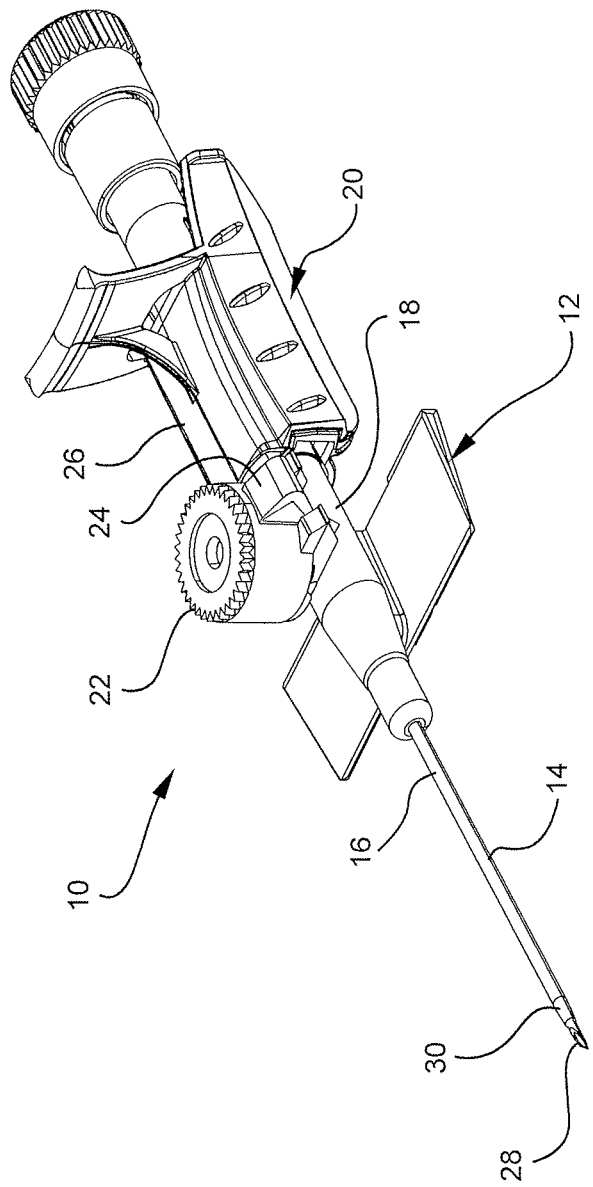
FIG. 1 is a perspective view of a extravascular system.

Referring to FIG. 1, a perspective view illustrates an example of an extravascular system 10 of multiple extravascular systems. In this example the extravascular system 10 includes a catheter assembly 12 and a needle assembly 20. The catheter assembly 12 includes a vascular access device, such as a catheter 14, partially housed within a catheter adapter 18. Also illustrated in FIG. 1 is a protection cap 22 positioned above the catheter adapter 18. The protection cap 22 may cover an access port which provides access into the catheter 14.

Figure 2:
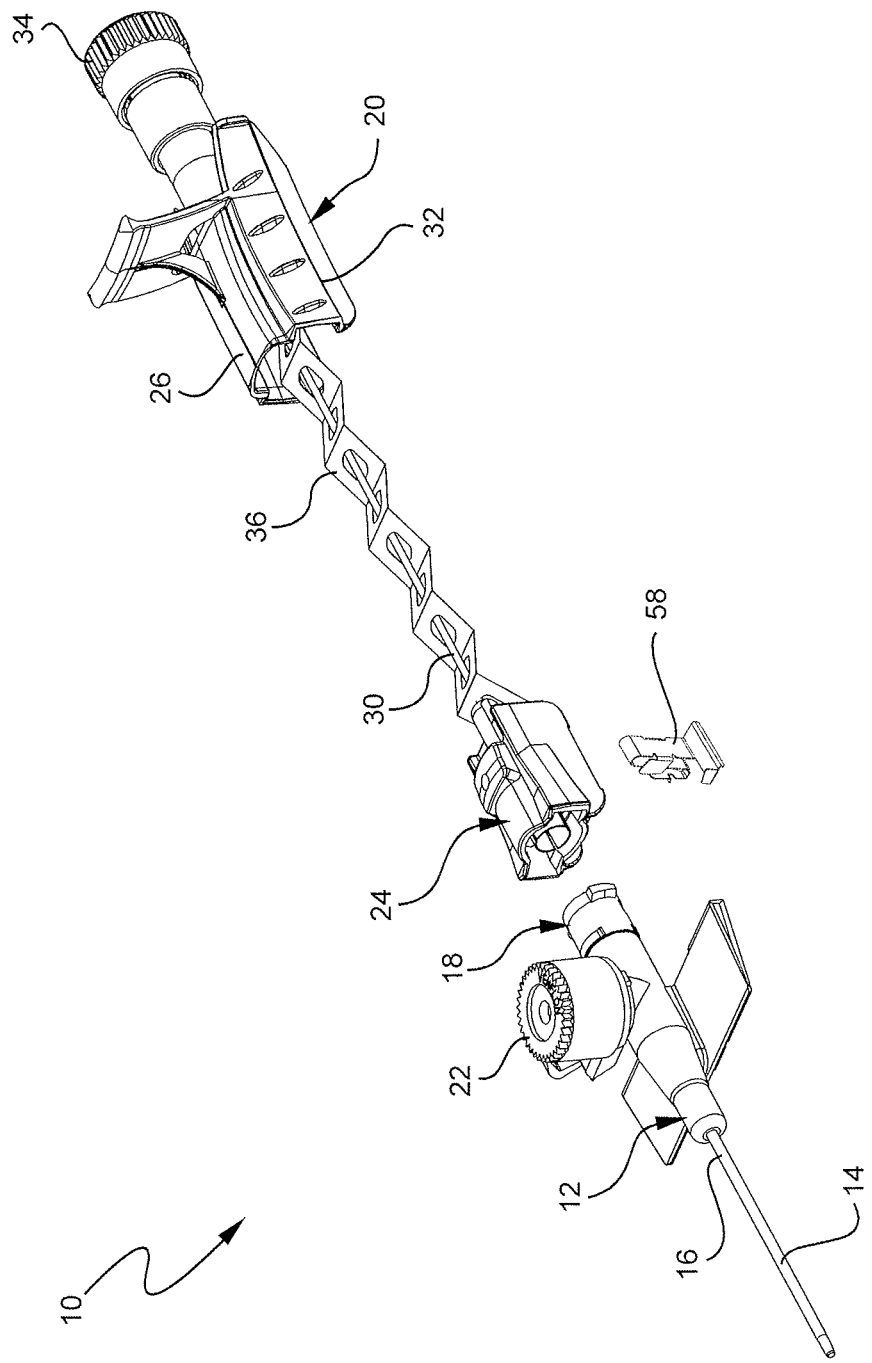
FIG. 2 is an exploded view of the extravascular system of FIG. 1.

Referring now to FIGS. 1 and 2, the extravascular system 10 also includes a needle assembly 20. The needle assembly includes a needle cap 24 and a needle hub 26. As can be seen by comparing FIGS. 1 and 2, the needle cap 24 and the tether 36 may be adapted to fit at least substantially inside the needle hub 26 when the needle assembly 20 is in the pre-use configuration. The needle assembly 20 may include additional parts or components adapted to provide the needle assembly 20 with the desired functionality. Similarly, the catheter assembly 12 may include additional or alternative parts and subcomponents depending on the configuration of the catheter assembly 12 and its intended usage.

The needle cap 24 is configured such that it will contain the needle tip 28 when the needle 30 is removed from the catheter 14. The needle assembly 20 is securely attached to the catheter adapter 18 thereby providing for manipulation of the needle 30 and placement of the catheter 14 within the vasculature of a patient. The needle assembly 20 may include grips 32 which allow for more secure gripping of the needle assembly 20 and maneuvering of the needle 30.

Referring now to FIG. 2, the extravascular system 10 is illustrated in an exploded view. As with FIG. 1, the catheter assembly 12 and needle assembly 20 are shown. As discussed above, the catheter assembly 12 includes a catheter 14 for placement within the vascular system of a patient. The catheter adapter 18 is configured such that the catheter 14 can be attached to further medical devices or tubing, such as for the administration of fluids to the patient. In that regard, the illustrated catheter assembly 12 also includes a protection cap 22 which covers an access port which provides further access to the catheter 14.

Also illustrated in FIG. 2 is the needle assembly 20 in a position in which the needle cap 24 has been fully separated from the catheter adapter 18. As mentioned above, the needle assembly 20 as illustrated includes grips 32 for use in retracting and manipulating the position of the needle 30.

Extending between the needle cap 24 and the needle hub 26 is a tether 36. The length of the tether 36 is selected such that when the needle cap 24 is maximally deployed from the needle hub 26 and the needle tip 28 of needle 30 is securely housed within the needle cap 24, the tether 36 is fully extended thereby preventing a separation of the needle cap 24 from the needle hub 26. Additionally, when the tether 36 is fully extended needle cap 24 is unable to be removed from the needle tip 28 thereby ensuring that the needle tip 28 remains safely contained within the needle cap 24. The tether 36 may be folded in an accordion configuration, may be straight, or take any other desired configuration.

As illustrated in FIG. 2, the needle tip 28 is secured within the needle cap 24. The tether 36 is in the extended position between the needle cap 24 and the needle hub 26. Thus, the needle 30 is prevented from being pulled out of the needle cap 24. The interior of the needle cap 24 also cooperates with structures on the needle (not shown) and the V-clip 58 to prevent the needle from moving forward out of the needle cap 24. The needle shield and/or V-clip 58 is illustrated in FIG. 2 in a contracted form; also illustrated is the clip housing cover 60, both of which are described in further detail below.

Figure 3:
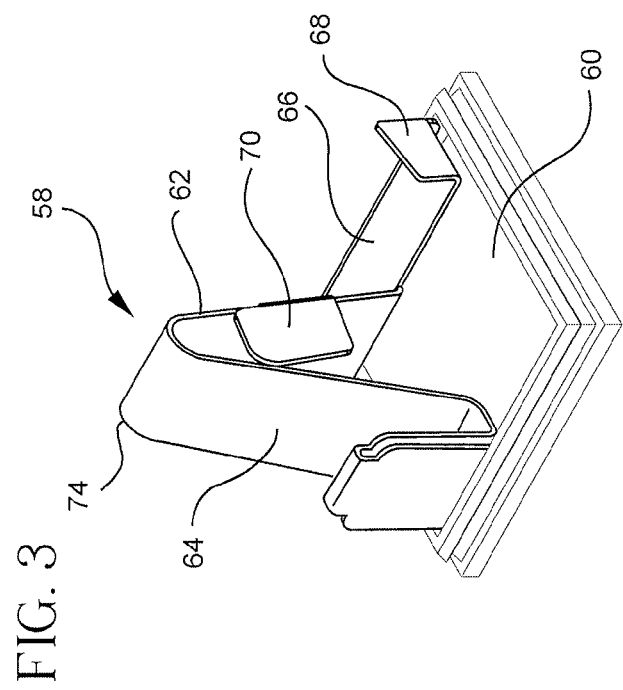
FIG. 3 is a perspective view of a V-clip shield with a clip housing cover.
Figure 4:
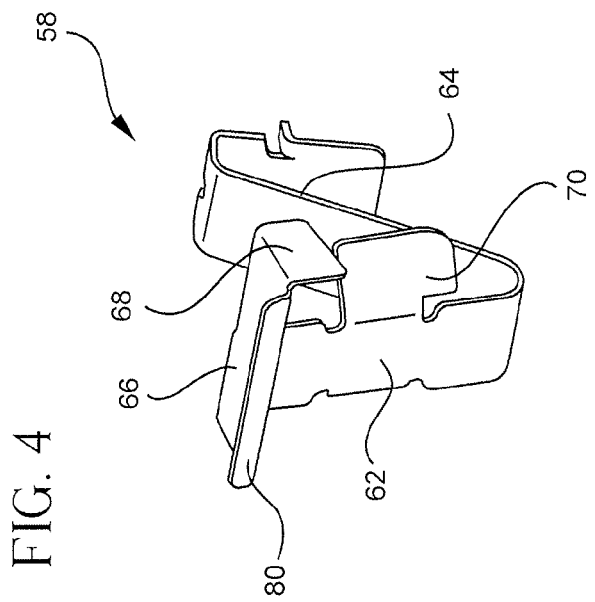
FIG. 4 is a perspective view of a V-clip shield.

Referring now to FIGS. 3 and 4, an example of a shield 58 for use with a needle cap 24 within an extravascular system 10 is shown in perspective view. The shield 58 is a V-clip having a first arm 62 and a second arm 64. The first arm 62 includes an extension 66 forming a pawl 68 at the end of the extension 66. The first arm 62 and/or the second arm 64 may also include a needle tip shield flap 70 capable of halting the advancement of the needle tip 28 after the V-clip 58 is engaged. The shield flap 70 is used to prevent the reemergence of the sharp needle tip 28 from the needle cap 24 after the needle 30 has been shielded by the cap 24.

Figure 5A:
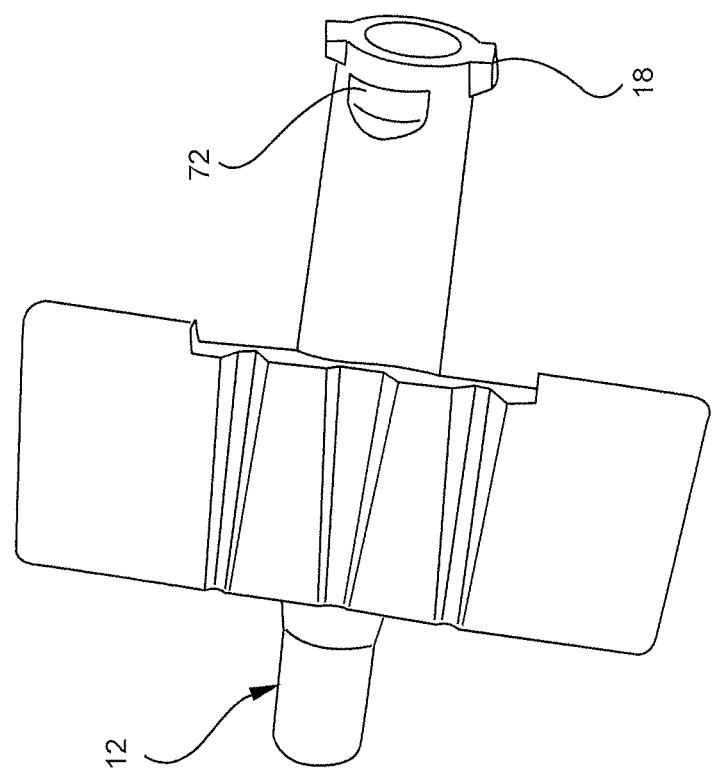
FIG. 5A is a perspective view of a catheter adapter having a groove.
Figure 5B:
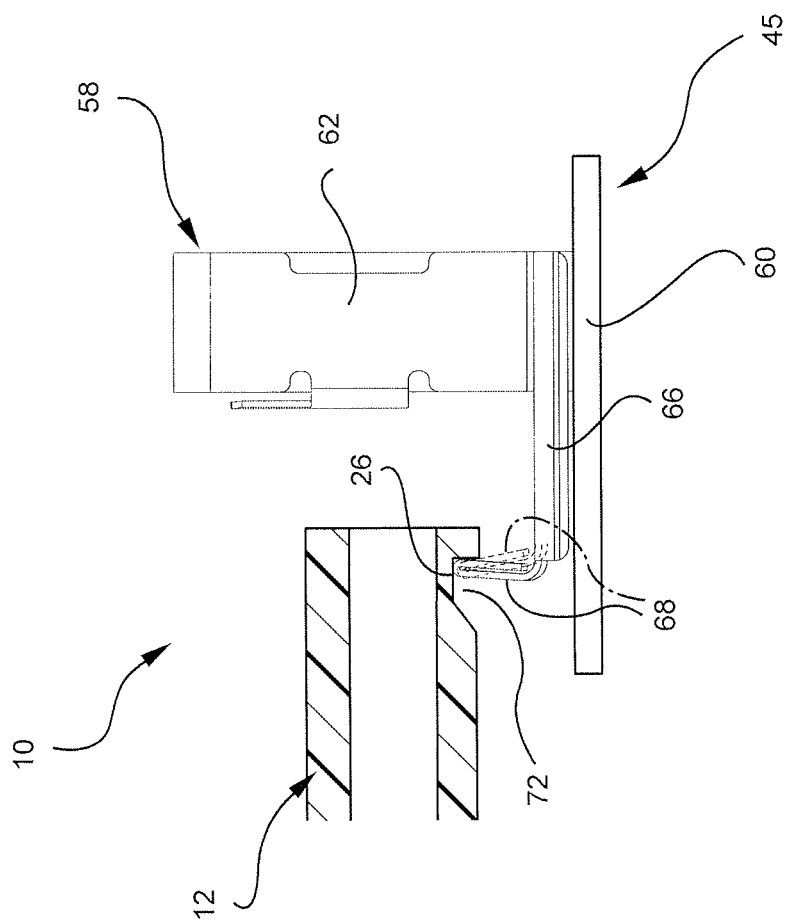
FIG. 5B is a cross section view of a V-clip shield pawl separating from a catheter groove.

The pawl 68 is formed of a metal that is bent at a primarily 90 degree bend from the extension 66. However, the pawl 68 may be bent at any other desired angle. For example, bends in the range of from about 90 degrees to about 70 degrees are presently preferred. The pawl 68 on the V-clip 58 serves to engage a crescent-shaped groove 72 on the catheter adapter 18 (see FIG. 5A). The pawl 68 engages the groove 72 to prevent the needle cap 24 from separating from the catheter adapter 18 until the needle 30 is withdrawn far enough to activate the V-clip 58. FIG. 5B illustrates a pawl 68 being separated from the groove 72.

Returning to FIGS. 3 and 4, when the V-clip 58 is activated, the first arm 62 will, under the spring force of an elbow 74, separate from the second arm 64. As the first arm 62 separates from the second arm 64, the pawl 68 will move from a first position to a second position. When the pawl 68 is in its first position, it is engaged with the groove 72 on the catheter adapter 18. After the pawl 68 moves from its first position to its second position, the pawl moves from engagement with the groove 72 to a position that is out of engagement with the groove 72.

In order to prevent premature disengagement of the pawl 68 from the groove 72, the pawl 68 must be of sufficient strength to avoid any bending, movement, shifting, or other action that would cause the V-clip 58 to separate from the catheter adapter 18 before the needle 30 has advanced far enough to activate or engage the V-clip 58. Various features and methods may be used to strengthen the pawl 68 and its relationship to the extension 66. Further, depending on the environment of vascular access devices and features thereof in which a pawl 68 is used, the pawl 68 may need to meet certain design requirements including size, shape, orientation, materials, and other features that would require additional pawl 68 strength.

Merely providing a pawl 68 with a thinner material will increase the likelihood that the pawl 68 will decouple from the groove 72. To prevent premature decoupling, one or more features may be included to strengthen the pawl 68. Such a feature may, for example, include decreasing the space between the V-clip housing cover 60 and the extension 66 so that the pawl 68 cannot rise to a height capable of disengaging the groove 72 (see FIG. 5B). Such feature may additionally or alternatively, for example, include a dent in the bend from the extension 66 or V-clip arm to the pawl 68.

Referring to FIG. 6, the pawl 68 of the V-clip 58 is shown having a dent 76 formed within the bend 78 between the pawl 68 and the extension 66. The dent 78 increases pawl 68 strength and prevents the pawl 68 from bending when separation force is placed between the pawl 68 and the groove 72, thus increasing the premature separation force required. By incorporating a dent 76 in the bend 78, a higher premature separation force is required, thus ensuring that the needle cap 24 does not separate prematurely from the catheter adapter 18 and thereby expose the clinician to an unprotected needle tip 28. The V-clip illustrated in FIG. 6 has a single dent 76. However, any number or configuration of dents 76 may be included and positioned at any desired location over the width of the pawl 68.

The extension 66 also includes a bend 80 along the length of the extension 66 to provide increased rigidity to the extension 66. Increased rigidity in the extension 66 will also help the pawl 68 avoid raising within the groove 72, resulting in premature decoupling.

Referring to FIG. 7, a bottom view of the pawl 68 reveals the underside of the dent 76 formed within the bend 78 between the pawl 68 and the extension 66 on the first arm. The dent 76 may be altered, supported, and/or replaced by any other feature capable of strengthening the bend 78 between the pawl 68 and the extension 66. Such alteration, replacement, or optimization may include modifying the parameters of depth, length, width, number of dents, and orientation of dents and/or other features. For example, a pawl 68 may fold back onto itself (see FIG. 10 and discussion below).

Figure 8:
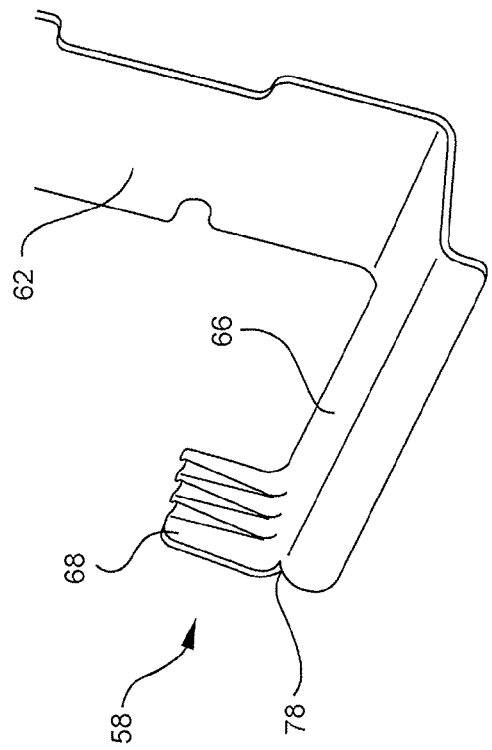
FIG. 8 is a bottom perspective view of a pawl folded inward at an angle less than 90°.

Referring to FIG. 8, a pawl 68 may fold in a direction towards the extension 66, causing the bend 78 to be formed at an angle less than 90 degrees. For example the bend may have an angle in the range of from about 70 degrees to about 90 degrees.

Figure 9:
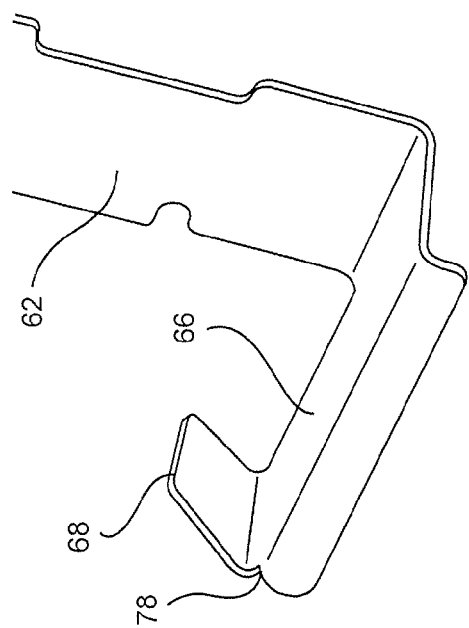
FIG. 9 is bottom perspective view of a pawl having a corrugated design.

As another example, and as shown in FIG. 9, a pawl 68 with a corrugated design may also result in the same strength increase seen with the dent 76. Such a corrugated design may provide equivalent strength as multiple dents being formed within the bend 78. By applying a corrugated shape it is possible increase the strength of the pawl and resists premature decoupling. A further advantage to the corrugated shape is to minimize axial movement of pawl in the space between the ridge on the needle cap and the groove edge on the catheter adapter. The corrugated shape may also provide a "spring" action keeping the needle cap 24 firmly in place in relation to the catheter hub 18. Finally, the corrugated shape helps prevent the risk of the pawl being stopped by burrs and sharp edges in the groove during opening of the V-clip 58.

By including a dent 76 or other similar strength-providing features, the bending strength of the pawl 68 is increased. This increase in bending strength of the pawl 68 is accomplished by lowering the point of bending to the end of the dent 76 or other feature (such as a brace). By lowering or otherwise moving the point of bending to the end of the dent 76 or other feature, a higher resistance to bending is created in the dented region. The location, length, shape, and/or size of the pawl 68 may be increased and/or decreased in order to adjust the premature separation force between the pawl 68 and the groove 72. For example, the dent 76 may preferably be placed in the center of the bend 78 to avoid torsional bending of the pawl 68 under stress.

The pawl 68 and/or its surrounding environment may also be modified in order to adjust the amount of play between the groove 72 of the catheter adapter 18 and the environment within the needle cap 24, to ensure that there is minimum play between the needle cap 24 and the catheter adapter 18 (such as the space shown in FIG. 5B between the extension 66 and the housing cover). By minimizing play, the premature separation force between the groove 72 and the pawl 68 will be maximized. In addition, the length or width of the portion of the pawl 68 which comes into contact with structure within or near the groove 72 is also important in controlling the premature separation force between the groove 72 and the pawl 68.

In addition, it may be desirable to expand the size of the pawl 68 in order to increase the contact area with the groove 26 on the catheter hub 18. This is another manner in which the contact area with the groove can be optimized which in turn resists premature decoupling. Further, the lower edge of the pawl can be optimized as required for particular catheter configurations to optimize the contact area for increased resistance to decoupling.

Figure 10:
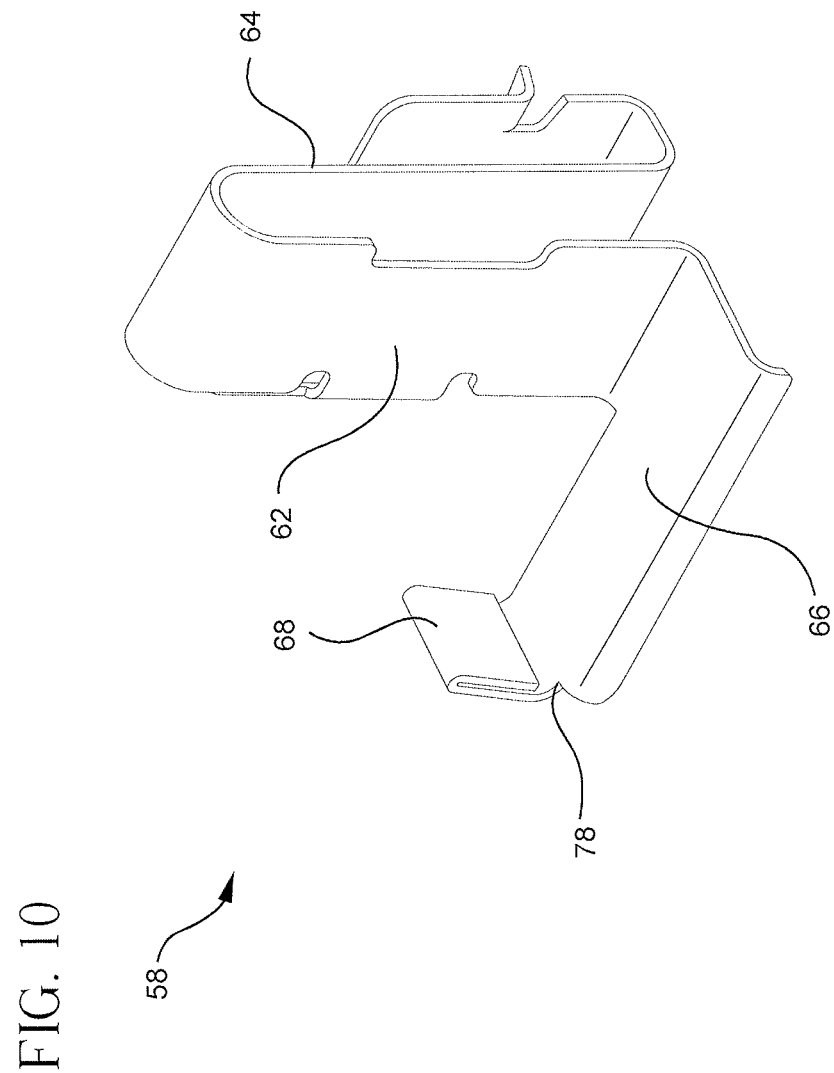
FIG. 10 is a bottom perspective view of a pawl folded back onto itself.

Finally, referring now to FIG. 10, a pawl 68 may be folded back onto itself. Indeed, the pawl 68 may be folded back on itself to form essentially a pawl 68 of double thickness. The pawl 68 of FIG. 10 may be accomplished by creating a template for a pawl that is twice the desired length of the final pawl 68 so that when the extended pawl is folded back onto itself a pawl 68 of double thickness is created and the pawl 68 is of a desired final length.

The present invention may be embodied in other specific forms without departing from its structures, methods, or other essential characteristics as broadly described herein and claimed hereinafter. The described embodiments are to be considered in all respects only as illustrative, and not restric- The invevtion claimed is:

1. A needle assembly comprising:
an introducer needle having a proximal end and a distal tip;
a needle hub in which the proximal end of the introducer needle is secured; and
a needle cap tethered to the needle hub to define a maximum spacing between the needle hub and needle cap, wherein, when at the maximum spacing, the distal tip of the introducer needle is contained within the needle cap, the needle cap including a V-clip needle shield for preventing the distal tip of the introducer needle from extending distally from the needle cap once the distal tip has been withdrawn proximally into the needle cap, the V-clip needle shield comprising:
a first arm;
a second arm coupled to the first arm via an elbow, the elbow having an unbiased position in which the first and second arms are spaced apart and a biased position in which the first arm is compressed towards the second arm;
an extension from the first arm, the extension extending distally beyond a distal edge of the first arm, a distal end of the extension being bent upwardly to form a pawl, at least one dent being formed within the bend to reinforce the bend, the pawl being oriented at an angle of approximately 70° from the extension arm wherein a distal end of the pawl is folded back towards the bend; and
a shield flap that extends inwardly from the first arm such that when the elbow is in the unbiased position, the shield flap is positioned between the first and second arms;
wherein, prior to withdrawing the distal tip of the introducer needle into the needle cap, the introducer needle is configured to force the first arm inwardly to cause the elbow to be in the biased position, and once the distal tip is withdrawn proximally past the first arm, the elbow returns to the unbiased position thereby causing the shield flap to block the distal tip of the introducer needle such that the distal tip cannot extend distally beyond the shield flap, the combination of the tether and the shield flap thereby maintaining the distal tip within the needle cap.

2. The needle assembly of claim 1, wherein the pawl is configured to couple the needle cap to a catheter adapter while the introducer needle extends into the catheter adapter.

3. The needle assembly of claim 1, wherein the needle hub is configured to contain the tether and at least a portion of the needle cap.

4. The needle assembly of claim 1, wherein the needle cap further comprises a clip housing cover having a surface on which the V-clip needle shield rests.

5. The needle assembly of claim 1, wherein an outer edge of the extension is bent to provide reinforcement to the extension.

6. An extravascular system comprising:
a catheter adapter; and
a needle assembly comprising:
an introducer needle having a proximal end and a distal tip;
a needle hub in which the proximal end of the introducer needle is secured; and
a needle cap tethered to the needle hub to define a maximum spacing between the needle hub and needle cap, wherein, when at the maximum spacing, the distal tip of the introducer needle is contained within the needle cap, the needle cap including a V-clip needle shield for preventing the distal tip of the introducer needle from extending distally from the needle cap once the distal tip has been withdrawn proximally into the needle cap, the V-clip needle shield comprising:
a first arm;
a second arm coupled to the first arm via an elbow, the elbow having an unbiased position in which the first and second arms are spaced apart and a biased position in which the first arm is compressed towards the second arm;
an extension from the first arm, the extension extending distally beyond a distal edge of the first arm, a distal end of the extension forming a pawl, the pawl comprising a first portion of the extension that is bent upwardly from the extension and a second portion of the extension that is bent downwardly against the first portion, the bend between the first portion and the extension including at least one dent to reinforce the bend; and
a shield flap that extends inwardly from the first arm such that when the elbow is in the unbiased position, the shield flap is positioned between the first and second arms;
wherein, prior to withdrawing the distal tip of the introducer needle into the needle cap, the introducer needle is configured to force the first arm inwardly to cause the elbow to be in the biased position, and when in the biased position, the pawl is coupled with a feature of the catheter adapter to prevent the needle cap from being removed from the catheter adapter, and once the distal tip is withdrawn proximally past the first arm, the elbow returns to the unbiased position thereby releasing the needle cap from the catheter adapter and causing the shield flap to block the distal tip of the introducer needle such that the distal tip cannot extend distally beyond the shield flap, the combination of the tether and the shield flap thereby maintaining the distal tip within the needle cap.

7. The extravascular system of claim 6, wherein the pawl is configured to insert into a groove in the catheter adapter.

8. The extravascular system of claim 6, wherein the needle hub is configured to contain the tether and at least a portion of the needle cap.

9. The extravascular system of claim 6, wherein an angle between the extension and the pawl is between 70° and 90°.

10. The extravascular system of claim 6, wherein the angle between the extension and the pawl is approximately 70°.

11. The extravascular system of claim 6, wherein the needle cap further comprises a clip housing cover having a surface on which the V-clip needle shield rests.

12. The extravascular system of claim 6, wherein an outer edge of the extension is bent to provide reinforcement to the extension.

13. An extravascular system comprising:
a catheter adapter; and
a needle assembly comprising:
an introducer needle having a proximal end and a distal tip;
a needle hub in which the proximal end of the introducer needle is secured; and a needle cap tethered to the needle hub to define a maximum spacing between the needle hub and needle cap, wherein, when at the maximum spacing, the distal tip of the introducer needle is contained within the needle cap, the needle cap including a V-clip needle shield for preventing the distal tip of the introducer needle from extending distally from the needle cap once the distal tip has been withdrawn proximally into the needle cap, the V-clip needle shield comprising:

a first arm;

a second arm coupled to the first arm via an elbow, the elbow having an unbiased position in which the first and second arms are spaced apart and a biased position in which the first arm is compressed towards the second arm;

an extension from the first arm, the extension extending distally beyond a distal edge of the first arm, a distal end of the extension forming a pawl, the pawl being corrugated to increase a thickness of the pawl; and a shield flap that extends inwardly from the first arm such that when the elbow is in the unbiased position, the shield flap is positioned between the first and second arms;

wherein, prior to withdrawing the distal tip of the introducer needle into the needle cap, the introducer needle is configured to force the first arm inwardly to cause the elbow to be in the biased position, and when in the biased position, the pawl is inserted into a groove in the catheter adapter to prevent the needle cap from being removed from the catheter adapter, and once the distal tip is withdrawn proximally past the first arm, the elbow returns to the unbiased position thereby releasing the needle cap from the catheter adapter and causing the shield flap to block the distal tip of the introducer needle such that the distal tip cannot extend distally beyond the shield flap, the combination of the tether and the shield flap thereby maintaining the distal tip within the needle cap.

* * * * *